US005618177A

United States Patent [19]
Abbott

[11] Patent Number: 5,618,177
[45] Date of Patent: Apr. 8, 1997

[54] ARRANGEMENT FOR FEEDING PRESSURIZED PARTICULATE MATERIAL

[75] Inventor: John D. Abbott, San Jose, Calif.

[73] Assignee: Dove Systems, Inc., Menlo Park, Calif.

[21] Appl. No.: 436,960

[22] Filed: May 8, 1995

[51] Int. Cl.$^6$ ...................................................... A61C 3/02
[52] U.S. Cl. ................................ 433/88; 451/90; 451/99; 222/161; 239/144
[58] Field of Search .............................. 433/88; 451/75, 451/90, 91, 99; 285/156; 222/161; 239/144, 311

[56] References Cited

U.S. PATENT DOCUMENTS

| 617,728 | 1/1899 | Farrey ........................... 285/156 |
|---|---|---|
| 1,664,369 | 3/1928 | Maurer ........................... 433/88 |
| 2,549,033 | 4/1951 | Tyrner ............................ 451/99 |
| 2,661,537 | 12/1953 | Angell ........................... 433/88 |
| 2,696,049 | 12/1954 | Black . | |
| 3,270,463 | 9/1966 | Ashworth et al. ............. 222/161 |
| 3,344,524 | 10/1967 | Kulischenko ................. 433/88 |
| 3,852,918 | 12/1974 | Black . | |
| 4,412,402 | 11/1983 | Gallant . | |
| 4,494,932 | 1/1985 | Rzewinski ..................... 451/99 |
| 4,522,597 | 6/1985 | Gallant .......................... 433/216 |
| 4,635,897 | 1/1987 | Gallant .......................... 251/5 |
| 4,708,534 | 11/1987 | Gallant .......................... 406/75 |
| 4,733,503 | 3/1988 | Gallant .......................... 51/410 |
| 4,893,440 | 1/1990 | Gallant et al. ............... 51/436 |
| 5,275,561 | 1/1994 | Goldsmith ..................... 433/29 |
| 5,330,354 | 7/1994 | Gallant .......................... 433/88 |
| 5,334,016 | 8/1994 | Goldsmith ..................... 433/29 |
| 5,350,299 | 9/1994 | Gallant .......................... 433/88 |

FOREIGN PATENT DOCUMENTS

WO93/10718  6/1993  WIPO .

OTHER PUBLICATIONS

"Technic for Nonmechanical Preparation of Cavities and Prophylaxis," Robert Black, Journal of the American Dental Association, vol. 32, pp. 955–965, 1945.
"Airbrasive: some Fundamentals," Robert Black, Journal of the American Dental Association, vol. 41, pp. 701–710, 1950.
"Airbrasive Technic Discussed," Harold Roach, Journal of the American Dental Association, vol. 43, p. 108, 1951.
"Analysis of airbrasive procedures in dental practice," Sidney Epstein, Journal of the American Denal Association, vol. 43, p. 578, 1951.
Advertisement: "MicroPrep™Cavity Preparation System," Sunrise Technologies, undated.

*Primary Examiner*—Cary E. O'Connor
*Attorney, Agent, or Firm*—Jeffrey Slusher

[57] ABSTRACT

A pressurized feeder vessel feeds powdered material into a stream of propellant gas. The feeder vessel includes a funnel-shaped hopper that is resiliently suspended by an elastic member inside the vessel. A vibrator such as an electric motor with an eccentric weight on its shaft vibrates the bottom end of the hopper. The vibration forces of the vibrator are preferably transferred to the hopper via a flexible diaphragm. The hopper is thus subjected to primary vibration forces and torques from below, and secondary, reaction vibration forces and torques from above. This induces the powder in the hopper to fluidize thoroughly and to circulate. In particular, it circulates over and past an inlet orifice, through which powder exits the hopper and enters the propellant stream. Powder circulation thus also prevents clogging of the inlet orifice and leads to more even flow rates. The invention is particularly well suited for delivering abrasive powder to a hand-held dental tool for abrasive treatment of teeth.

7 Claims, 5 Drawing Sheets

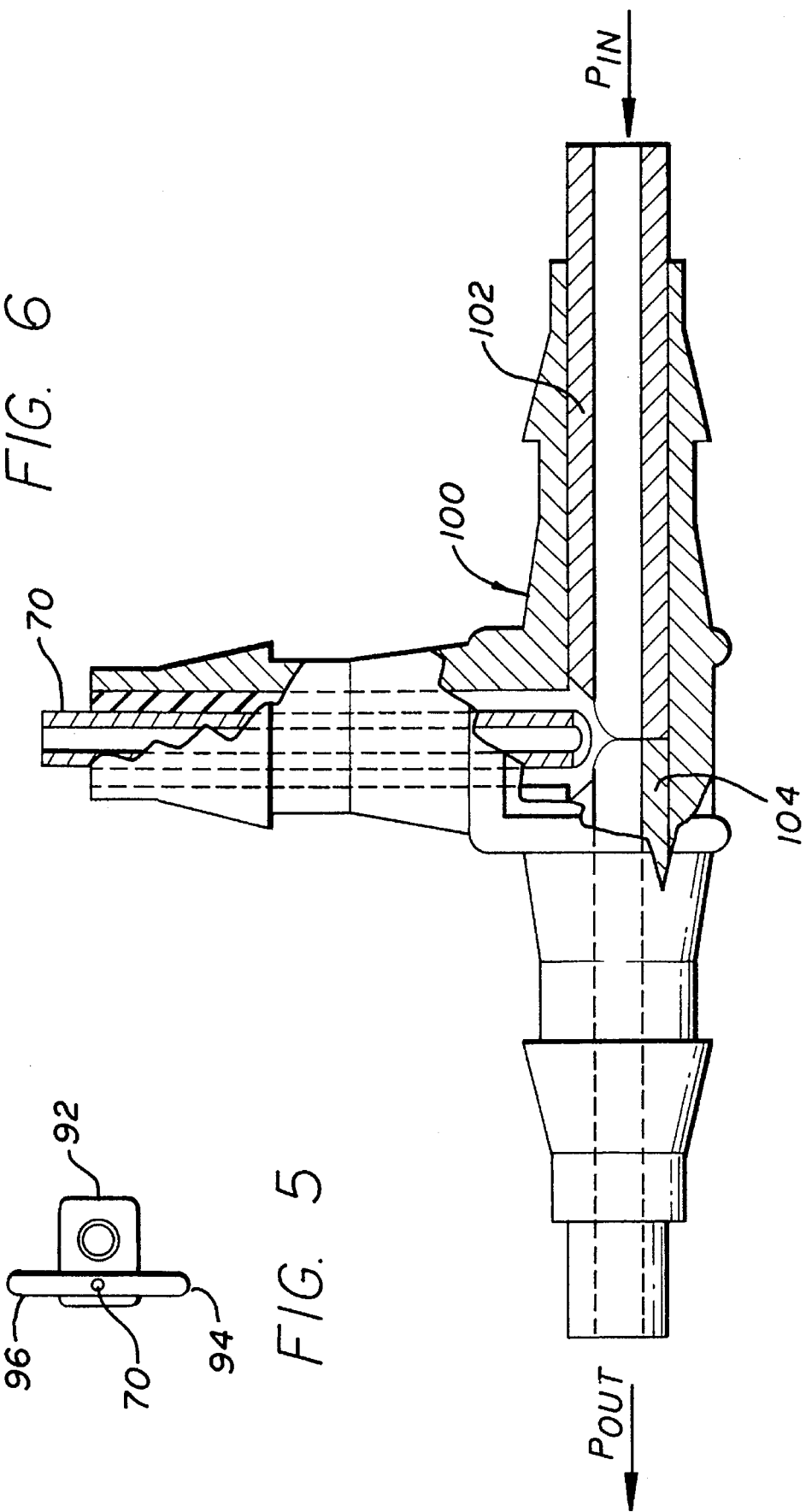

ARRANGEMENT FOR FEEDING PRESSURIZED PARTICULATE MATERIAL

BACKGROUND OF THE INVENTION

1. Field of the Invention

This invention involves an arrangement for smooth and continuous feeding of pressurized blasting material, in particular, for feeding blasting powder in abrasive dental devices.

2. Description of the Related Art

The whine of the dentist's drill is one of the most unwelcome sounds in the modern world. A standing goal in dentistry is therefore to find a way to efficiently and precisely reduce a tooth, for example, in preparation for a filling, or to remove plaque, with as little discomfort to the patient as possible.

One promising alternative to the conventional rotating or vibrating mechanical drill bit is a tool that directs a fine stream of a pressurized abrasive powder against the surface of the tooth. Experience has indicated that these devices cause much less trauma to the tooth yet are at least as effective at removing tooth enamel as a conventional drill head. Moreover, since there is no hard physical contact between the surface of the tooth and a fast-vibrating or rotating drill bit or head, blasting systems also reduce the risk of chipping the tooth surface.

The general technique of treating teeth using an abrasive jet is described in the following publications:

"Technic for Nonmechanical Preparation of Cavities and Prophylaxis," Robert Black, Journal of the American Dental Association, Vol. 32, pp. 955–965, 1945;;

"Airbrasive: some fundamentals," Robert Black, Journal of the American Dental Association, Vol. 41, pp. 701–710, 1950;

"Airbrasive Technic Discussed," Harold Roach, Journal of the American Dental Association, Vol. 43, p. 108, 1951; and "Analysis of airbrasive procedures in dental practice," Sidney Epstein, Journal of the American Dental Association, Vol. 43, p. 578, 1951.

Known devices for treating teeth with an abrasive jet include those described in:

U.S. Pat. No. 2,696,049 (Black, Dec. 7, 1954);
U.S. Pat. No. 3,852,918 (Black, Dec. 10, 1974);
U.S. Pat. No. 4,412,402 (Gallant, Nov. 1, 1983);
U.S. Pat. No. 4,522,597 (Gallant, Jun. 11, 1985);
U.S. Pat. No. 4,635,897 (Gallant, Jan. 13, 1987);
U.S. Pat. No. 4,708,534 (Gallant, Nov. 24, 1987);
U.S. Pat. No. 4,733,503 (Gallant, Mar. 29, 1988);
U.S. Pat. No. 4,893,440 (Gallant et al., Jan. 16, 1990);
U.S. Pat. No. 5,275,561 (Goldsmith, Jan. 4, 1994);
U.S. Pat. No. 5,330,354 (Gallant, Jul. 19, 1994);
U.S. Pat. No. 5,334,016 (Goldsmith, Aug. 2, 1994);
U.S. Pat. No. 5,350,299 (Gallant, Sep. 27, 1994); and
International (PCT) Patent Application, Publication No. WO 93/10718 (Goldsmith, published Jun. 10, 1993).

Known devices such as these suffer from one or all of the following disadvantages:

1) their delivery rates vary greatly depending on how full their reservoirs are, which in turn means they are harder to control accurately;

2) they don't keep the blasting material, such as abrasive powder, properly stirred and fluidized (in the device described in auger-fed U.S. Pat. No. 4,708,534 device, for example, big particles may tend to remain in the vessel);

3) they have many parts, which makes them hard to manufacture and expensive; and 4) they are not self-cleaning, so that feeding nozzles often become clogged.

What is needed is a feeding device that overcomes these disadvantages.

SUMMARY OF THE INVENTION

An arrangement for delivering powdered material under pressure includes a source of pressurized propellant gas and a pressure vessel that is connected to the gas source via a pressure inlet. A mainly funnel-shaped hopper is mounted within the pressure vessel, and holds the powdered material. An inlet orifice opens into the region holding powder in the hopper; powder exits the hopper through the inlet orifice and enters a pressurized outlet line. In dental applications, a hand-held tooth abrasion tool or pick is connected to the outlet line to receive the pressurized powder, such as aluminum oxide, that flows from the pressure vessel. A suspension resiliently supports the hopper within the pressure vessel.

A vibrator, such as a rotary or reciprocating electric motor, applies oscillatory forces and torques to the bottom portion of the hopper and thereby causes the powdered material in the hopper to fluidize and circulate within the hopper and across the inlet orifice. In particular, the hopper is shaped such that the powder flows substantially straight across the inlet orifice to prevent and relieve clogging.

In one embodiment, the suspension is an annular elastic member that contacts the hopper around the top portion of the hopper. The elastic member is fastened to an inner surface of the pressure vessel, preferably via an annular retention band that is secured to the inside surface of the pressure vessel.

In the preferred embodiment, a bottom assembly is attached to the bottom portion of the hopper, and one end of a bracket is attached to the bottom assembly. The vibrator in this embodiment is an electric rotary or reciprocating motor that is mounted on a second end of the bracket off-axis with respect to a central axis of the hopper. The bracket is connected at its first end to the bottom portion of the hopper via a resilient diaphragm member. The resilient diaphragm member is seated in a sleeve, which is attached to the bottom portion of the hopper. All connection between the vibrator and the hopper thereby runs via the resilient diaphragm member.

In the preferred embodiment, an upper cap is secured, for example, by mating threads, to an upper end of the pressure vessel and has a substantially conical inner surface and a central opening. A lid-like plug member is spring-biased upward to close and seal the central opening. A detent member limits downward travel of the plug member within the pressure vessel. When the plug member is depressed, the pressure vessel is unsealed and powdered material on the conical inner surface of the upper cap can flow into the pressure vessel around the plug member.

A T-shaped pressure connector is also provided. This connector has three branches—a vertical branch and two horizontal branches. A single horizontal bore extends through the horizontal branches and a vertical bore extends through the vertical branch and opens into the horizontal bore. The inlet orifice is a metal tube forming a nozzle and is secured in the vertical branch. A tubular metallic insert is secured in each horizontal branch to form respective connections for the pressure inlet and the pressurized outlet. Lower, inner end portions of the tubular metallic inserts substantially abut each other directly under an inner opening of the vertical branch and nozzle. Upper, inner end portions of the tubular metallic inserts are rounded and, together, form a funnel region for receiving the powdered material that enters the pressure connector through the nozzle.

BRIEF DESCRIPTION OF THE DRAWINGS

FIG. 5 is a bottom view of a pressure connector used in one embodiment of the invention.

FIG. 6 is an enlarged, partially cut-away view of an alternative pressure connector.

DETAILED DESCRIPTION

Figure 1:
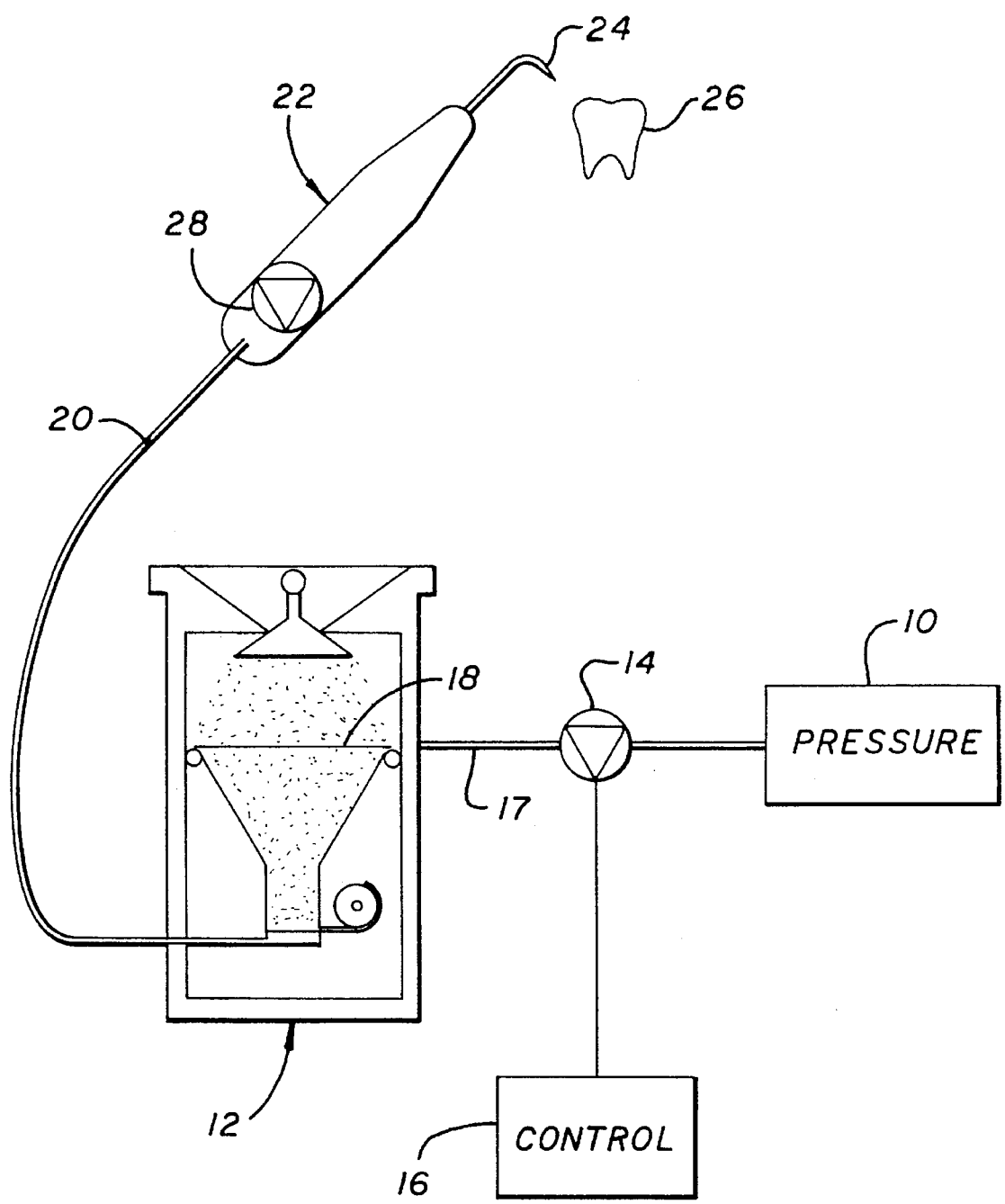
FIG. 1 shows the main components of a system for treatment of teeth using an abrasive powder.

FIG. 1 shows the main components of a system for treatment of teeth using an abrasive powder. These include a conventional pressure source 10, which delivers pressurized, propellant gas such as air or nitrogen, possibly mixed with anaesthetic gases. The propellant gas enters a fluidizing pressure vessel or feeder 12 by way of a valve 14, whose setting is controlled either manually or automatically by a conventional controller or regulator 16, and an inlet hose or tube.

The feeder 12 includes a hopper or other reservoir of abrasive material 18, which it delivers under pressure through an outlet tube 20 to a hand-held blasting tool 22. The tool 22 typically includes a metal nozzle 24 though which the abrasive material is propelled as a high-speed jet against the surface of a tooth 26. The hand-held tool 22 preferably also includes a valve 28 with a button or other actuator that the dentist can operate to control or shut-off the delivery of blasting material to the tooth.

The invention effectively delivers a wide range of particles under pressure. Any abrasive particles may be used according to the invention as long as they are fine enough to be fluidized and delivered in a propellant gas. Aluminum oxide is the generally preferred material for the abrasive treatment of teeth, and the invention is particularly advantageous for delivering this material, since it doesn't clog and has a very even delivery rate. The invention is not limited to use in the field of dentistry, however; it could, for example, be used for the precise and powerful delivery of other abrasive particles, for example, for etching glass, and even for general dispensing of powdered chemicals, not just abrasive powders. For the sake of simplicity only, the invention is described below in the context of delivering an abrasive material and all such materials and particles are referred to below as the abrasive "powder".

Figure 2:
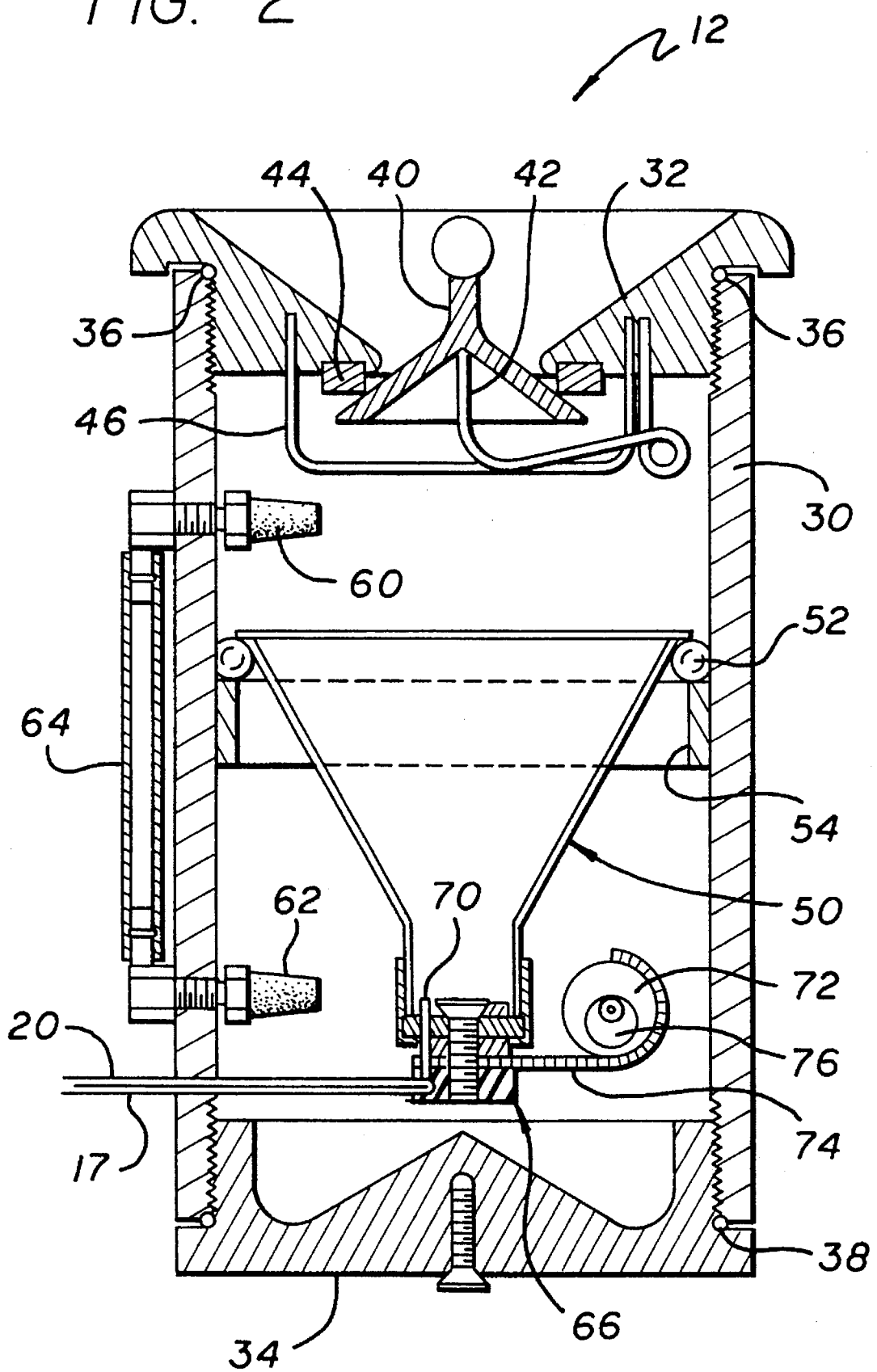
FIG. 2 is a cross-sectional view of a preferred embodiment of the pressurization and feeding arrangement according to the invention.

FIG. 2 is a cross-sectional view of a preferred embodiment of the feeder 12 according to the invention. The feeder 12 includes a generally cylindrical main wall 30, an upper cap 32, and a lower cap 34. The upper and lower caps are preferably removable from the main wall 30 to allow for cleaning. For ease of assembly and removal, the caps preferably screw onto the wall 30, and to prevent loss of internal pressure they preferably seal against the wall by means of respective O-rings or gaskets 36, 38. Other means of secure attachment are also possible, such as clamps or mating flanges, such as are found, for example, on pressure cookers.

The upper cap 32 preferably angles down to a central opening to form a funnel- or hopper-like surface. The central opening is closed and sealed off by a plug member 40. The plug member 40 is preferably conical and Seals the central opening of the upper cap under the force of a spring 42, which presses the plug member upward against an annular gasket or ring 44. Downward travel of the plug member is preferably limited by a wire or other stop 46 that extends under the plug member. In order to fill the feeder with abrasive powder, the user simply pushes down on the plug member 40 and pours the abrasive into the funnel-like portion of the upper cap. The powder then runs down around the edge of the plug member and into the feeder under the force of gravity. The user then releases the plug member, which then seats against the gasket 44 to seal the interior of the feeder. Although such a spring-biased plug is very convenient in that it makes for quick filling, it is also possible to do without any form of plug and simply to unscrew the upper cap every time one wants to fill the feeder.

A funnel or cone member 50 is mounted below the central opening of the upper cap 32 such that powder that is poured into the upper cap falls down into the funnel. The funnel thus forms a reservoir for the powder. The funnel is preferably mainly conical, such that its cross-section is mainly linear, Since such funnels are easy to manufacture and are best at allowing powder to "slide" downward; the funnel may, however, also be concave or convex. The cone member 50 is preferably suspended substantially coaxial with the cylindrical main wall 30 via an annular elastic member 52, which is securely attached, for example using epoxy or some other known adhesive, to and around the upper edge or lip of the cone 50. A retaining ring or band 54 is preferably attached to the inside surface of the wall 30 to provide a support on which the elastic member 52 and funnel 50 can rest and be securely fastened.

Filtered opening fittings 60, 62 preferably extend through the wall 30 above and below the upper edge of the funnel 50, respectively. The fittings 60, 62 are then connected by external tubing 64 to equalize the pressure on either side of the funnel.

Figure 3:
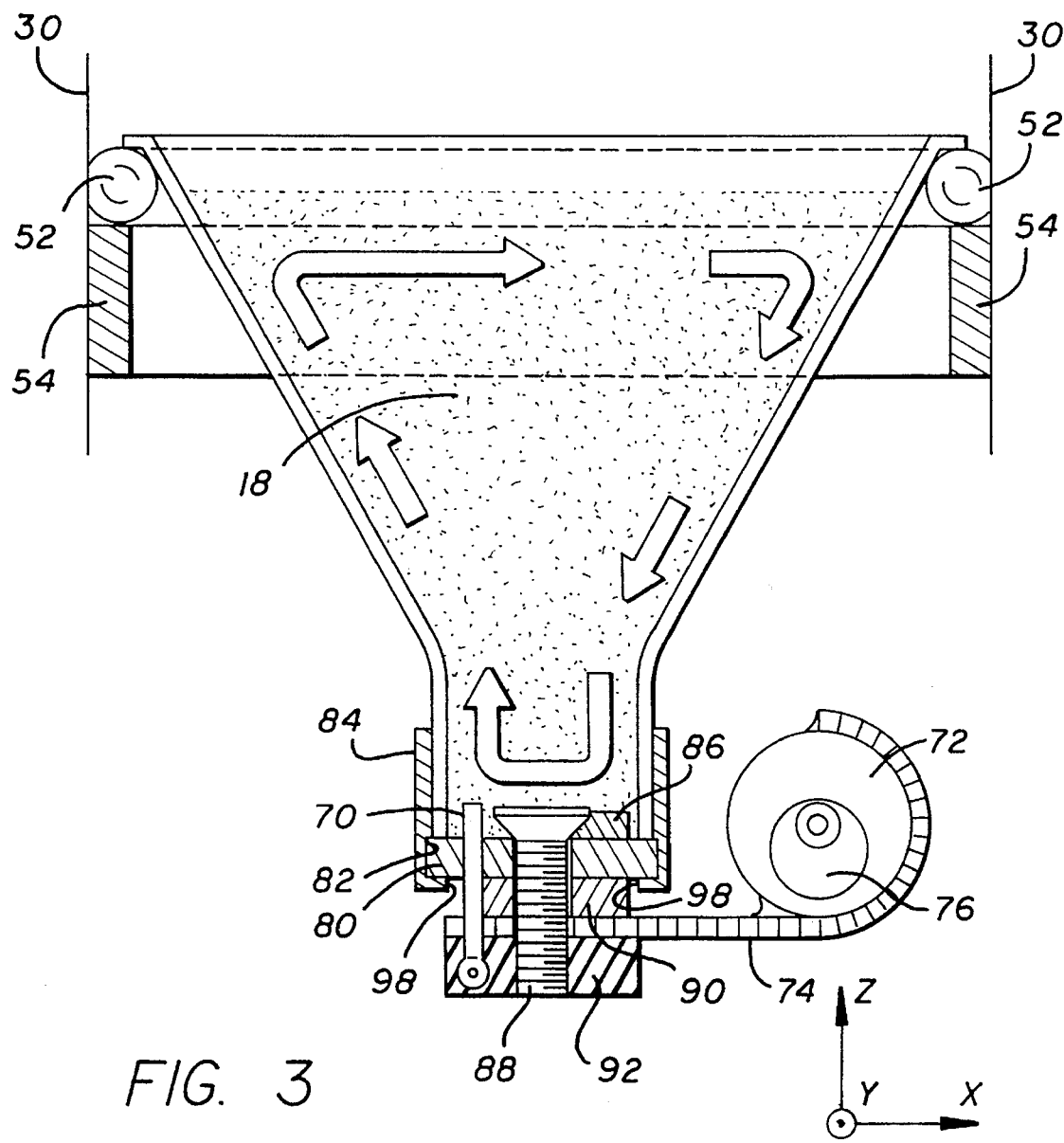
FIG. 3 is an enlarged view of a self-cleaning, fluidizing assembly according to the invention.

The bottom opening of the funnel 50 is sealed by a bottom diaphragm assembly 66 (described in greater detail below) through which an inlet nozzle 70 extends. Abrasive powder is drawn (mostly by gravity) down into the inlet nozzle 70, where it is caught up in the pressurized propellant gas that is delivered via the pressure inlet tube 17 and is forced out through the outlet tube 20. The openings in the wall 30 through which the tubes 17, 20 pass are sealed in any conventional way. A vibrator 72 is also mounted to the bottom assembly 66 of the funnel 30, preferably by a bracket or plate 74. The vibrator is preferably simply glued or soldered to the bracket, as is shown in FIG. 3. The bracket 74 is preferably metallic, such as an aluminum or steel strip, and should be rigid enough to transfer with little loss vibrational forces of the motor 72 as torques to the bottom assembly.

In the preferred embodiment, the vibrator 72 is a small, electric rotary motor with an eccentric weight or cam 76 mounted on its shaft. The axis of rotation of the motor shaft, and therefore of the cam, is preferably horizontal and off the vertical axis of the funnel. The assembly acts as a motor pick-up so that vibrations of the vibrator 72 are transferred to the bottom of the funnel as oscillatory positive-negative torques. Such small motors are readily available, are cheap but reliable, draw little current, and one can easily and accurately regulate their shaft rotation rates using known potentiometer-based actuators, which are easily incorporated into knobs, pedals, and slides. For any given application, however, if one knows through testing that there is an optimum speed, it is also possible to wire the motor for driving it at this fixed, optimum speed. The power source for the motor may be any conventional device and is therefore not shown in the figures. The vibrator may also be implemented using other devices such as solenoids, piezoelectric vibrators, and pneumatic vibrators.

In the case of piezoelectric devices as the vibrator, these may be attached directly to or near the bottom of the funnel 50, which can then be made of metal. This implementation, however, will typically be more expensive but no more efficient than the preferred embodiment shown in the figures.

With both caps 32, 34 attached to the main wall 30, and with the plug 40 seated against the inner edge of the central opening of the upper cap 32, the structure forms a pressure vessel. The wall 30 and caps 32, 34 are preferably made of a metal such as aluminum or steel that is easy to machine (for the threading by which the caps are secured), easy to clean, resists abrasion, and can withstand without leakage and significant deformation the internal pressure of the feeder. The plug member 40 is preferably made of a similar material, but since it will normally be subjected to less potential abrasion and is easier to replace, it may also be made of sufficiently abrasion-resistant and rigid plastic.

FIG. 3 is an enlarged cross-sectional view of the cone 50, its upper, resonant supporting structure (the elastic member 52 and the band 54) and the bottom assembly 66. Large arrows in FIG. 3 indicate the circulating motion of the powder 18 when the motor 72 is running.

The cone 50 must be highly abrasion-resistant and it should have a low enough mass that it creates the "wave action" (described below) that gives rise to the circulation of the powder 18; it should furthermore create as little noise as possible. Nylon, UHMW, and other conventional plastics have been found suitable. It is also possible to make the cone of metals such as anodized aluminum, or to chrome-plate other metals.

The elastic member 52 is preferably of silicon rubber, which provides adequate strength, resiliency, and long life. Other elastic materials may, however, be used; the key feature is that the elastic member must allow resonant vibrations to occur in the funnel so that the powder fluidizes and circulates. It is also possible to injection-mold the elastic member 52 as a part of the upper lip of the cone itself, or to weaken the upper lip of the cone 50 (for example, by molding it thinner) such that the lip itself is flexible enough to create the circulating wave action. Furthermore, it is not necessary for the cone to be suspended from the top— intermediate or bottom suspension is also possible, as long as the cone is resiliently suspended within the pressure vessel. Conventional testing and observation will determine whether these alternative structures provide proper circulation. As is explained in greater detail below, the resilient suspension of the cone 50, for example, using the elastic member 52, creates a resonant structure.

Figure 4:
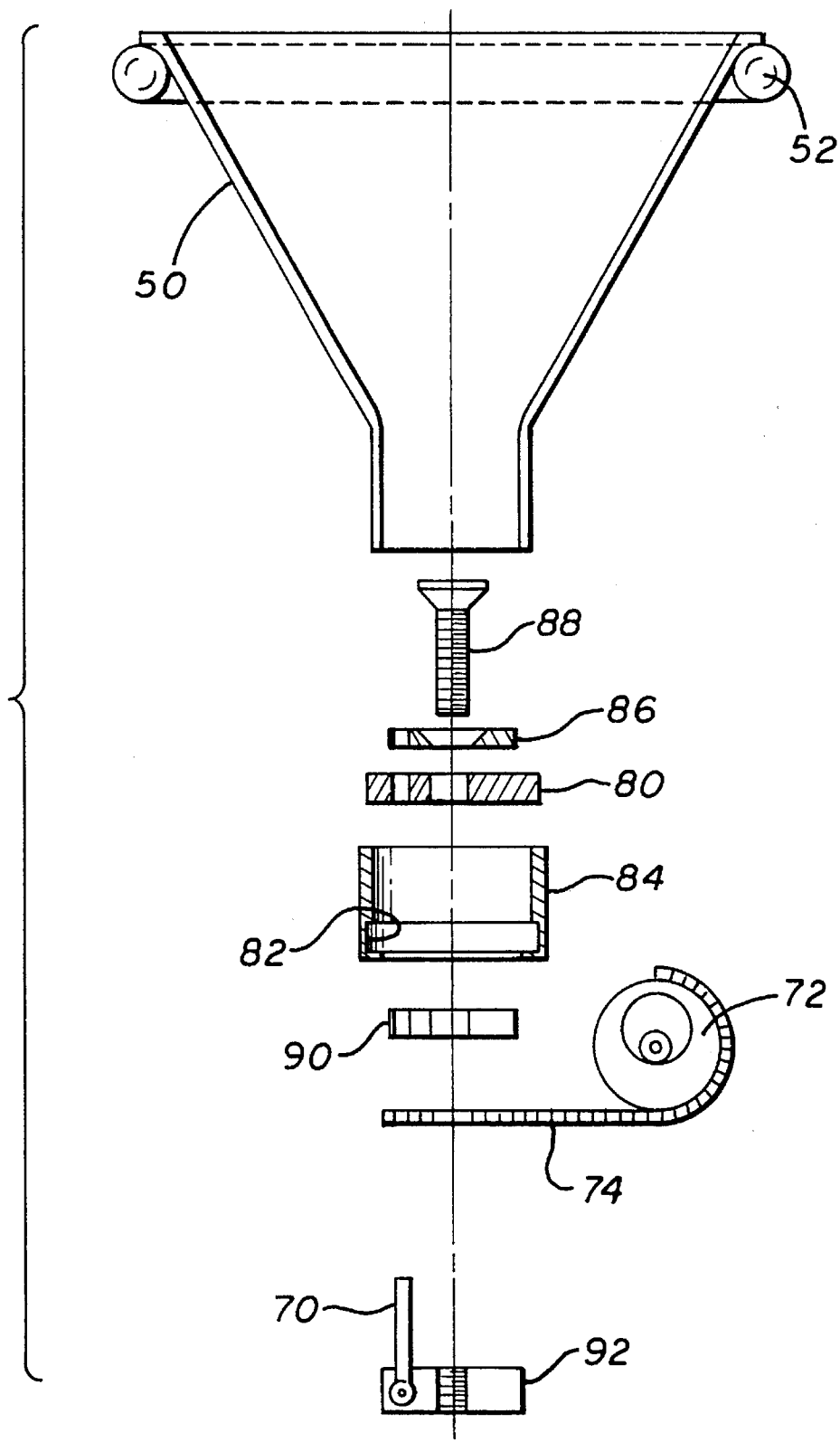
FIG. 4 is an exploded view of the assembly shown in FIG. 3.

FIG. 4 shows the entire cone assembly (cone 50, elastic member 52, and bottom assembly 66) in an exploded view. An annular, elastic diaphragm 80 seats in a recess 82 in a sleeve 84, and is held in place in the sleeve by a metal diaphragm washer 86. A screw 88 extends through the washer 86, through a hole in the center of the diaphragm 80, through the mainly open bottom of the sleeve 84, though a metal bracket washer 90, through a hole in the bracket 66, and into a metal locking block 92. Tightening the screw down into the locking block 92 holds the bottom assembly together. Note that the inlet nozzle 70 also extends upward through corresponding holes in the locking block 92, the bracket 66, both washers 86, 90, and the diaphragm 80. The diaphragm washer 86 is preferably countersunk so that the head of the screw 88 does not extend into and disrupt the path of the circulating powder.

The inlet nozzle 70 preferably extends a short distance above the upper surface of the diaphragm washer 86 so that it is just in the circulating flow of powder. Making the nozzle as a separate, tube-like metal member, for example, of carbide, also allows for smooth flow of powder through the nozzle; it is also easier to assemble, manufacture, and clean. The nozzle forms an effective orifice through which the powder can exit the "hopper", that is, the funnel 50, which serves as a powder reservoir. It is, however, possible to replace the nozzle with a simple hole through all the remaining elements of the bottom assembly, although this would lead to difficulties of alignment and an increased tendency to clog.

The sleeve 84 is securely fastened over the bottom end of the funnel member 50. For ease of assembly and disassembly, the sleeve preferably has internal threading, which either mates with corresponding external threading molded into the outer surface of the bottom portion of the funnel 50, or simply cuts into the synthetic material of the funnel itself. It is also possible to glue the sleeve onto the funnel.

The diaphragm 80 is preferably made of silicon rubber with a vinyl coating, since this material is resilient and self-lubricating, which prevents powder from sticking to it. As FIG. 3 shows, the diaphragm 80 is held below by an inward-extending flange at the bottom of the sleeve 84. Note, however, that there is preferably an annular gap 98 between the bracket washer 90 and the innermost edge of the flange. Experiments have shown that this gap is not strictly necessary to create the circulation of powder, but that it improves both the degree of fluidization and the speed of circulation of the powder.

In other words, experiments have indicated :that the best fluidization and circulation of the powder is achieved when the funnel 50 and diaphragm do not form a single, rigid, resonant body. It is, however, possible to make the bottom portion of the funnel itself somewhat weaker and elastic (for example, thinner), doing without the diaphragm altogether (replacing it by the weakened, elastic portion of the funnel), as long as the central portion of the funnel is more rigid than its top and bottom mounting portions. This alternative solution, however, makes it more difficult to mount the bottom assembly securely onto the funnel and it deliberately weakens the structure.

For ease of reference, an X-Y-Z axis is shown in FIG. 3, with the Y axis extending into the plane of the figure. In the illustrated embodiment, the axis of rotation of the motor extends in the Y-direction.

When the motor 72 is running, the rotation of the eccentric weight 76 causes forces that lie predominantly in the X-Z plane. Some direct oscillating forces in the X- and Z-directions are thus applied to the base of the funnel 50, but these forces are transferred by the elastic diaphragm 80 (assuming there is the gap 98). Because the motor is mounted off-axis with respect to the funnel, however, X- and Z-direction forces are also at least partially transferred as oscillating torque about the Y-axis; this torque is also applied through the diaphragm to the bottom of the funnel. Corresponding reaction forces and torques arise at the top edge of the funnel via the elastic member 52. In other words, a high-speed, oscillatory bending of the funnel occurs, with primary vibration of the funnel at its bottom end and secondary vibration of the funnel at its upper edge.

The vibratory forces in the funnel are transferred by friction to the powder. The inventor has discovered that this action sets up a standing wave in the powder in the funnel, with circulating particle movement as indicated by the large arrows in FIG. 3. In other words, the high-speed (preferably on the order of several hundred or a few thousands of r.p.m.s for the motor 72), oscillatory torque applied at the bottom and top of the funnel sets up a dominant resonant mode within the funnel that causes the abrasive particles not only to fluidize substantially completely, but also to circulate within the funnel. Notice that the entire feeder or "hopper" area, that is, the entire funnel 50, is vibrated, which prevents powder from sticking to any part of the interior wall.

The circulation of the powder has at least four advantageous effects. First, the powder remains fluidized so that it flows properly and smoothly into the inlet nozzle 70. Second, smooth inlet flow provides a much more uniform flow and delivery rate than is possible using known devices. Third, the powder remains well mixed.

Fourth, the invention reduces or eliminates the problem of clogging, which is a great concern since the orifice through which the abrasive particles enter the nozzle is, in dental applications, typically no greater than from 0.38 mm to about 0.66 mm (0.015 to 0.026 inches). In the base of the funnel (within the area surrounded by the sleeve 84), the abrasive particles tend to flow straight across the inlet opening, that is, perpendicular to the nozzle. This in turn prevents the inlet opening from becoming clogged, since particles that otherwise may have a tendency to get stuck in the opening are swept along in the flow of particles, and those that have gotten stuck are quickly dislodged by the force of the particle "wave" flowing past the nozzle. This also improves the ability of the invention to deliver powder at a more uniform rate.

FIG. 5 is a bottom view of the locking block 92 used in one prototype of the invention. (See also FIG. 3.) A horizontal hole is drilled through the block and a vertical hole is drilled down through the block, opening into the horizontal hole. The nozzle 70 is inserted into the vertical hole and connecting tubing of metal or hard plastic is inserted into each side of the horizontal hole. The pressurized propellant gas line is connected to one horizontal connecting tube 94 and the outlet tube is connected to the other 96. As abrasive particles fall into the nozzle and down into the block 92, they are propelled out of the pressure vessel in the conventional manner. Note that the entire interior of the pressure vessel is at substantially the same high pressure as the propellant gas; the only outlet to a region of lower pressure is through the outlet tube for abrasive particles.

FIG. 6 shows an alternative embodiment of a pressure connector 100 that can be used in the invention. In this embodiment, the connector is made of hard plastic, preferably of nylon. The connector has three "arms" or "branches": two opposing horizontal branches and one vertical branch. The interior of the connector thus forms a T-shaped channel. Carbide or other hard metal inserts 102, 104 are inserted into the horizontal branches to provide strength, abrasion-resistance and rigidity. The nozzle is preferably also formed as a carbide insert. The branches are preferably barbed to enable secure and tight attachment of the inlet and outlet tubes.

The inner ends of the horizontal carbide inserts 102, 104 are preferably rounded at the portions that abut the bottom end of the nozzle. This allows them to form a small "funnel," which promotes effective, smooth flow of the abrasive powder into the stream of pressurized propellant gas. The bottom portions of the inserts preferably abut one another with little or no gap in order to minimize the amount of powder at rest that might otherwise build up there. The inner diameter of the horizontal branches in one prototype of the invention was approximately 1.23 mm (0.048 inches).

I claim:

1. An arrangement for delivering powdered material under pressure comprising:

A. a source of pressurized propellant gas;
   B. a pressure vessel that is connected to the source of pressurized propellant gas via a pressure inlet and that has a pressurized outlet;
   C. a mainly funnel-shaped hopper that is mounted within the pressure vessel, that holds the powdered material, and that has a top portion and a bottom portion;
   D. an inlet orifice through which the powdered material exits the hopper and enters the pressurized outlet line;
   E. a suspension resiliently supporting the hopper within the pressure vessel; and
   F. a vibration means for applying oscillatory forces and torques to the bottom portion of the hopper and thereby for causing the powdered material in the hopper to fluidize and circulate within the hopper and across the inlet orifice;
   in which the suspension is an annular elastic member that contacts the hopper around the top portion of the hopper and is fastened to an inner surface of the pressure vessel.

2. An arrangement for abrasive treatment of teeth with pressurized abrasive powder comprising:

A. a source of pressurized propellant gas;
   B. a pressure vessel that is connected to the source of pressurized propellant gas via a pressure inlet and that has a pressurized outlet line;
   C. a hand-held tooth abrasion tool connected to the pressurized outlet line and receiving the powdered material mixed with the pressurized propellant gas;
   D. a mainly funnel-shaped hopper that is mounted within the pressure vessel, that holds the powdered material, and that has a top portion and a bottom portion;
   E. an inlet nozzle that extends and opens into the powdered material in the hopper, and through which the powdered material exits the hopper and enters the pressurized outlet line;
   F. a suspension resiliently supporting the hopper at its upper portion;
   G. a vibration means for applying oscillatory forces and torques to the bottom portion of the hopper and thereby for causing the powdered material in the hopper to fluidize and circulate within the hopper and across the inlet orifice;
   H. a bottom assembly that is attached to the bottom portion of the hopper;

I. a bracket that is attached at a first end to the bottom assembly;

in which:

J. the suspension is an annular elastic member that contacts the hopper around the top portion of the hopper and is fastened to an inner surface of the pressure vessel;

K. the vibration means includes an oscillatory motor that is mounted on a second end of the bracket off-axis with respect to a central axis of the hopper;

L. the bracket is connected at its first end to the bottom portion of the hopper via a resilient diaphragm member; and M. the resilient diaphragm member is seated in a sleeve, which is attached to the bottom portion of the hopper, all connection between the vibration means and the hopper thereby being via the resilient diaphragm member.

3. An arrangement for delivering powdered material under pressure comprising:

A. a source of pressurized propellant gas;

B. a pressure vessel that is connected to the source of pressurized propellant gas via a pressure inlet and that has a pressurized outlet;

C. a mainly funnel-shaped hopper that is mounted within the pressure vessel, that holds the powdered material, and that has a top portion and a bottom portion;

D. an inlet orifice through which the powdered material exits the hopper and enters the pressurized outlet line;

E. a suspension resiliently supporting the hopper within the pressure vessel;

F. a vibration means for applying oscillatory forces and torques to the bottom portion of the hopper and thereby for causing the powdered material in the hopper to fluidize and circulate within the hopper and across the inlet orifice;

G. a bottom assembly that is attached to the bottom portion of the hopper; and

H. a bracket that is attached at a first end to the bottom assembly;

in which:

I. the vibration means includes an oscillatory motor that is mounted on a second end of the bracket off-axis with respect to a central axis of the hopper.

4. An arrangement as in claim 3, in which the inlet orifice is a nozzle that extends and opens into the powdered material in the hopper.

5. An arrangement as in claim 3, in which the bracket is connected at its first end to the bottom portion of the hopper via a resilient diaphragm member.

6. An arrangement as in 5, in which the resilient diaphragm member is seated in a sleeve, which is attached to the bottom portion of the hopper, all connection between the vibration means and the hopper thereby being via the resilient diaphragm member.

7. An arrangement for delivering powdered material under pressure comprising:

A. a source of pressurized propellant gas;

B. a pressure vessel that is connected to the source of pressurized propellant gas via a pressure inlet and that has a pressurized outlet;

C. a mainly funnel-shaped hopper that is mounted within the pressure vessel, that holds the powdered material, and that has a top portion and a bottom portion;

D. an inlet orifice through which the powdered material exits the hopper and enters the pressurized outlet line;

E. a suspension resiliently supporting the hopper within the pressure vessel;

F. a vibration means for applying oscillatory forces and torques to the bottom portion of the hopper and thereby for causing the powdered material in the hopper to fluidize and circulate within the hopper and across the inlet orifice;

G. a pressure connector that has three branches—a vertical branch and two horizontal branches—in which:

a single horizontal bore extends through the horizontal branches;

a vertical bore extends through the vertical branch and opens into the horizontal bore;

the inlet orifice is a metal tube forming a nozzle that is secured in the vertical branch;

a tubular metallic insert is secured in each horizontal branch forming respective connections for the pressure inlet and the pressurized outlet;

lower, inner end portions of the tubular metallic inserts substantially abut each other directly under an inner opening of the vertical branch and nozzle; and upper, inner end portions of the tubular metallic inserts are rounded and, together, form a funnel region for receiving the powdered material that enters the pressure connector through the nozzle.

* * * * *